US006391644B1

(12) United States Patent
Gottlieb

(10) Patent No.: US 6,391,644 B1
(45) Date of Patent: May 21, 2002

(54) IMAGE ANALYSIS OF URINE

(76) Inventor: Dan Gottlieb, 1 Aharoni Street, Rehovot (IL), 76281

( * ) Notice: Subject to any disclaimer, the term of this patent is extended or adjusted under 35 U.S.C. 154(b) by 0 days.

(21) Appl. No.: 09/232,528

(22) Filed: Jan. 18, 1999

(30) Foreign Application Priority Data

Nov. 4, 1998 (IL) .................................................. 126881

(51) Int. Cl.$^7$ ............................................ G01N 33/493
(52) U.S. Cl. .............................. 436/63; 436/4; 436/811
(58) Field of Search ................................ 436/63, 4, 811

(56) References Cited

U.S. PATENT DOCUMENTS

| | | |
|---|---|---|
| 4,025,307 A | 5/1977 | Randolph et al. |
| 4,183,729 A | 1/1980 | Randolph |
| 4,263,010 A | 4/1981 | Randolph |
| 4,399,003 A | 8/1983 | Sarig et al. |
| 4,888,182 A | 12/1989 | Pak |
| 5,064,765 A | 11/1991 | Karasikov et al. |
| 5,122,284 A | * 6/1992 | Braynin et al. .............. 210/782 |
| 5,325,169 A | * 6/1994 | Nakamoto et al. ............ 356/73 |
| 5,741,648 A | * 4/1998 | Hemstreet, III et al. ......... 435/6 |
| 5,891,733 A | * 4/1999 | Inoue .......................... 436/63 |
| 6,004,821 A | * 12/1999 | Levine et al. ............... 436/169 |

* cited by examiner

Primary Examiner—Jill Warden
Assistant Examiner—Monique T. Cole
(74) Attorney, Agent, or Firm—Darby & Darby

(57) ABSTRACT

Apparatus for indicating the propensity of a subject to formation of urinary stones comprising apparatus for optically observing a urine sample from a subject under magnification and an image analyzer operative to determine the existence of crystalline bodies in the urine sample and to provide an output indication thereof.

7 Claims, 6 Drawing Sheets

Microfiche Appendix Included
(2 Microfiche, 153 Pages)

| Time | Total blobs | Valid blobs | Area | Perimeter | Compactness | Number of Holes | Roughness | Length | Breadth | Brightness |
|---|---|---|---|---|---|---|---|---|---|---|
| 18:59:7 | 2 | 2 | 51.50 | 31.49 | 1.53 | 0 | 1.06 | 11.11 | 4.63 | 10375.50 |
| 19:04:13 | 2 | 2 | 51.00 | 32.49 | 1.65 | 0 | 1.07 | 12.03 | 4.22 | 10407.00 |
| 19:09:20 | 2 | 2 | 44.00 | 28.78 | 1.50 | 0 | 1.05 | 9.88 | 4.51 | 9487.50 |
| 19:14:27 | 2 | 2 | 46.00 | 30.07 | 1.57 | 0 | 1.06 | 10.73 | 4.30 | 9704.50 |
| 19:19:33 | 2 | 2 | 45.00 | 29.78 | 1.57 | 0 | 1.06 | 10.66 | 4.23 | 9543.00 |

*ATTENTION:*

*[X] effective inhibition of crystallization of calcium oxalate in sampled urine*

*[ ] ineffective inhibition of crystallization of calcium oxalate in sampled urine*

IMAGE ANALYSIS OF URINE

FIELD OF THE INVENTION

The present invention relates to determination of the propensity of a subject to formation of urinary stones.

BACKGROUND OF THE INVENTION

It is estimated that approximately four percent of the adult population, worldwide, encounters a urinary stone difficulty.

Prophylactic treatment is known for preventing the occurrence of urinary stones. What is lacking is an efficient and cost-effective technique for screening the population in order to indicate those persons requiring prophylactic treatment.

Various techniques have been proposed for determining the propensity of a subject to formation of urinary stones. The following U.S. Patents are considered to represent the state of the art: U.S. Pat. Nos. 4,025,307; 4,183,729; 4,263,010; 4,399,003; 4,888,182 & 5,064,765.

SUMMARY OF THE INVENTION

The present invention seeks to provide an efficient and cost-effective technique and system for indicating the propensity of a subject to formation of urinary stones.

There is thus provided in accordance with a preferred embodiment of the present invention apparatus for indicating the propensity of a subject to formation of urinary stones including apparatus for optically observing a urine sample from a subject under magnification and an image analyzer operative to determine the existence of crystalline bodies in said urine sample and to provide an output indication thereof.

There is also provided in accordance with a preferred embodiment of the present invention apparatus for analyzing urine of a subject including:

apparatus for optically observing a urine sample from a subject under magnification; and an image analyzer operative to determine the existence of bodies in the urine sample and to provide an output indication thereof.

The bodies may include at least one of cells, crystalline bodies, microorganisms and casts.

Preferably, the image analyzer is also operative to provide an indication of the size of the crystalline bodies.

In accordance with a preferred embodiment of the present invention, the apparatus for optically observing is operative to observe at least one urine sample in the presence of at least one reagent.

Preferably, the apparatus for optically observing a urine sample is operative to observe a plurality of urine samples from a subject in the presence of a plurality of different reagents.

In accordance with a preferred embodiment of the present invention, the plurality of different reagents comprise crystallization inducers of different activities.

Preferably, the plurality of different reagents comprise crystallization inducers of different concentrations.

In accordance with a preferred embodiment of the present invention, the at least one reagent comprises a crystallization inducer.

In accordance with a preferred embodiment of the present invention, the image analyzer includes software which measures the mass of the bodies.

Additionally or alternatively, in accordance with a preferred embodiment of the present invention, the image analyzer includes software which indicates the shape of the bodies.

Additionally or alternatively, in accordance with a preferred embodiment of the present invention, the image analyzer includes software which indicates changes in the bodies over time.

There is also provided in accordance with a preferred embodiment of the present invention a method for indicating the propensity of a subject to formation of urinary stones comprising:

optically observing a urine sample from a subject under magnification; and performing computerized image analysis to determine the existence of crystalline bodies in the urine sample and to provide an output indication thereof.

There is additionally provided in accordance with a preferred embodiment of the present invention a method for analyzing urine of a subject comprising:

optically observing a urine sample from a subject under magnification; and performing image analysis to determine the existence of bodies in the urine sample and to provide an output indication thereof.

BRIEF DESCRIPTION OF THE DRAWINGS

The present invention will be more fully appreciated from the following detailed description in which.

BRIEF DESCRIPTION OF APPENDIX

Appendix A is a microfiche appendix containing two sheets of microfiche and 153 frames and contains a hexadecimal dump of software employed in accordance with a preferred embodiment of the present invention.

DETAILED DESCRIPTION OF A PREFERRED EMBODIMENT

Figure 1:
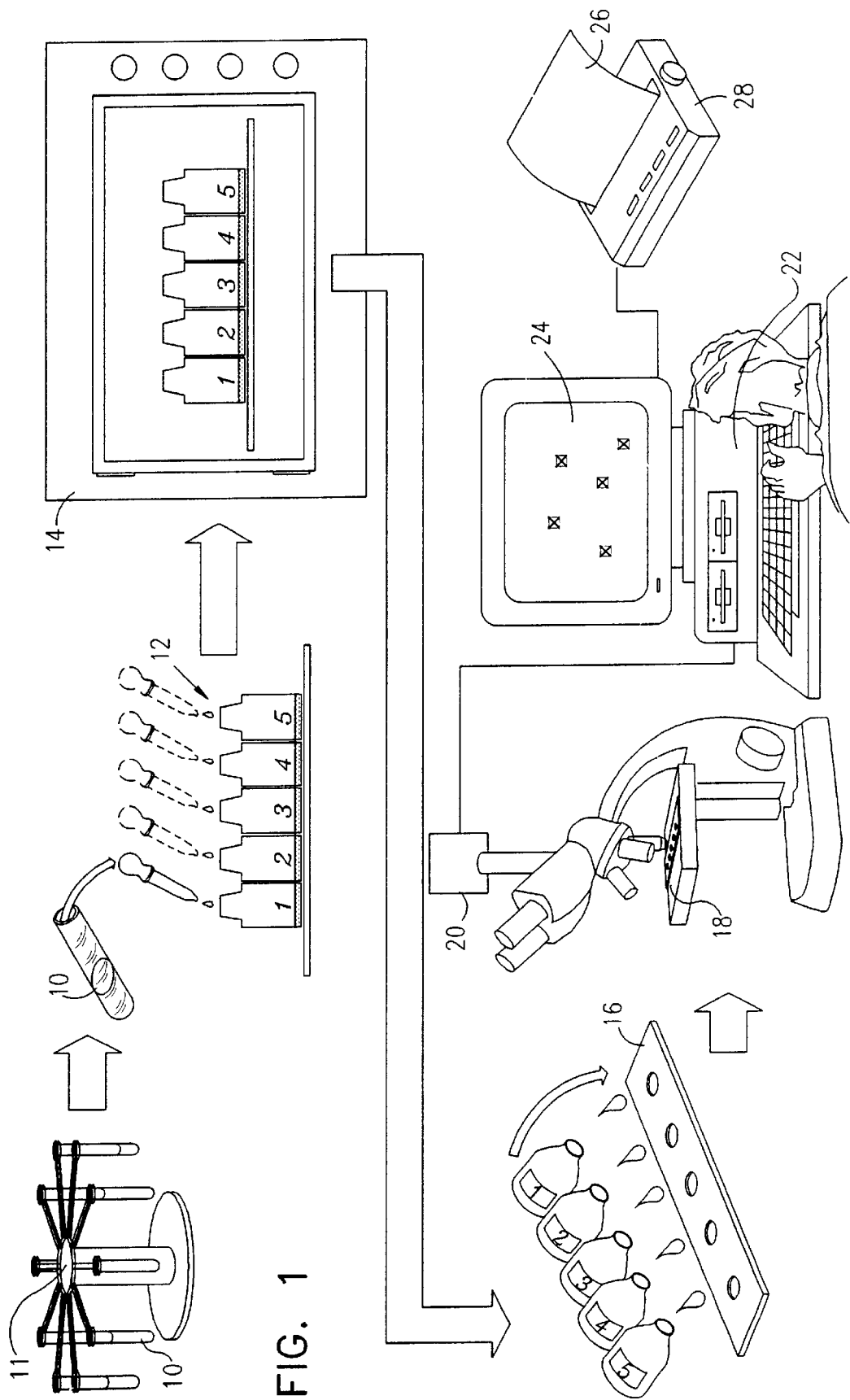
FIG. 1 is a simplified pictorial illustration of a system and method for analyzing urine of a subject which is particularly useful for indicating the propensity of a subject to formation of urinary stones in accordance with a preferred embodiment of the present invention.
Figure 3:
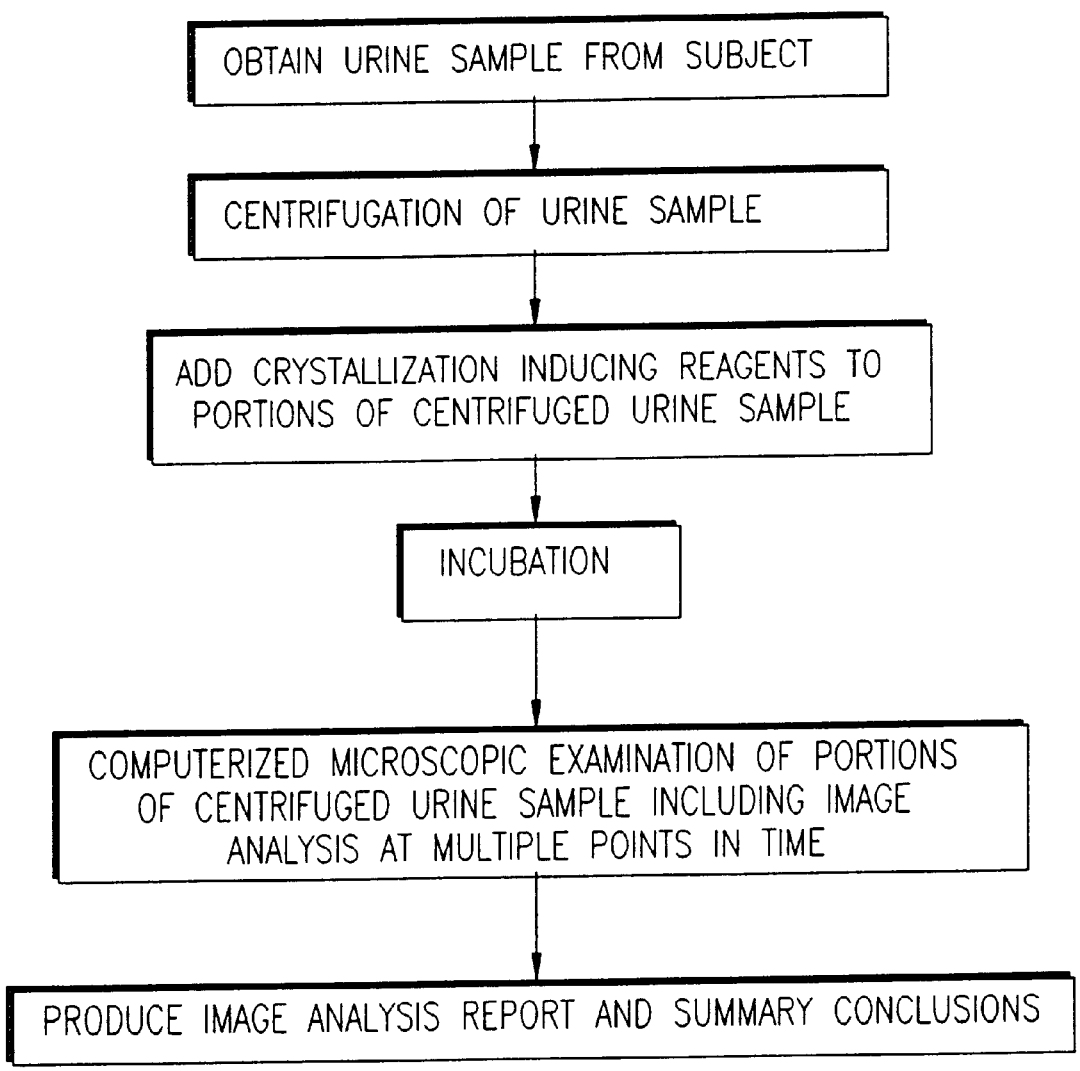
FIG. 3 is a simplified flowchart illustrating principal functional features of image analysis performed by the system and method of FIG. 1.

Reference is now made to FIGS. 1 and 3, which are respectively a simplified pictorial illustration and a flow chart of a system and method for analyzing urine of a subject which is particularly useful for indicating the propensity of a subject to formation of urinary stones in accordance with a preferred embodiment of the present invention.

The present invention, illustrated generally in FIGS. 1 and 3, seeks to provide an efficient and cost-effective technique and system for indicating the propensity of a subject to formation of urinary stones. As seen in FIG. 1, a sample of urine 10 received from a subject is centrifuged in a centrifuge 11 and thereafter preferably added dropwise to a plurality of containers 12, here numbered 1–5, each containing a reagent which enhances crystallization of calcium oxalate salts in the urine.

In accordance with a preferred embodiment of the present invention, the reagent comprises natrium-oxalate in different concentrations. Typically, the concentrations in containers 1–5 are as follows 0.5 milliMole/L, 2.5 milliMole/L, 10.0 milliMole/L, 25.0 milliMole/L & 50.0 milliMole/L respectively.

The containers 12, containing the reagents and the urine samples are preferably incubated in an incubator 14 at a temperature of 37 degrees Centigrade for a duration of about 30 minutes. Thereafter a drop from each of the containers is placed on a slide 16 which is placed under a microscope 18 which is equipped with a video camera 20.

The output of the video camera 20 is supplied to a computer 22, such as a PC which is equipped with suitable image analysis software, such as Matrox Inspector software, commercially available from Matrox Electronic Systems Ltd. of Dorval, Quebec, Canada together with special purpose software, preferably that presented in Appendix A. An image analysis output, preferably indicating the propensity of a subject to formation of urinary stones, may be provided on a display 24 or in hard copy form 26 by using a printer 28.

Figure 2:
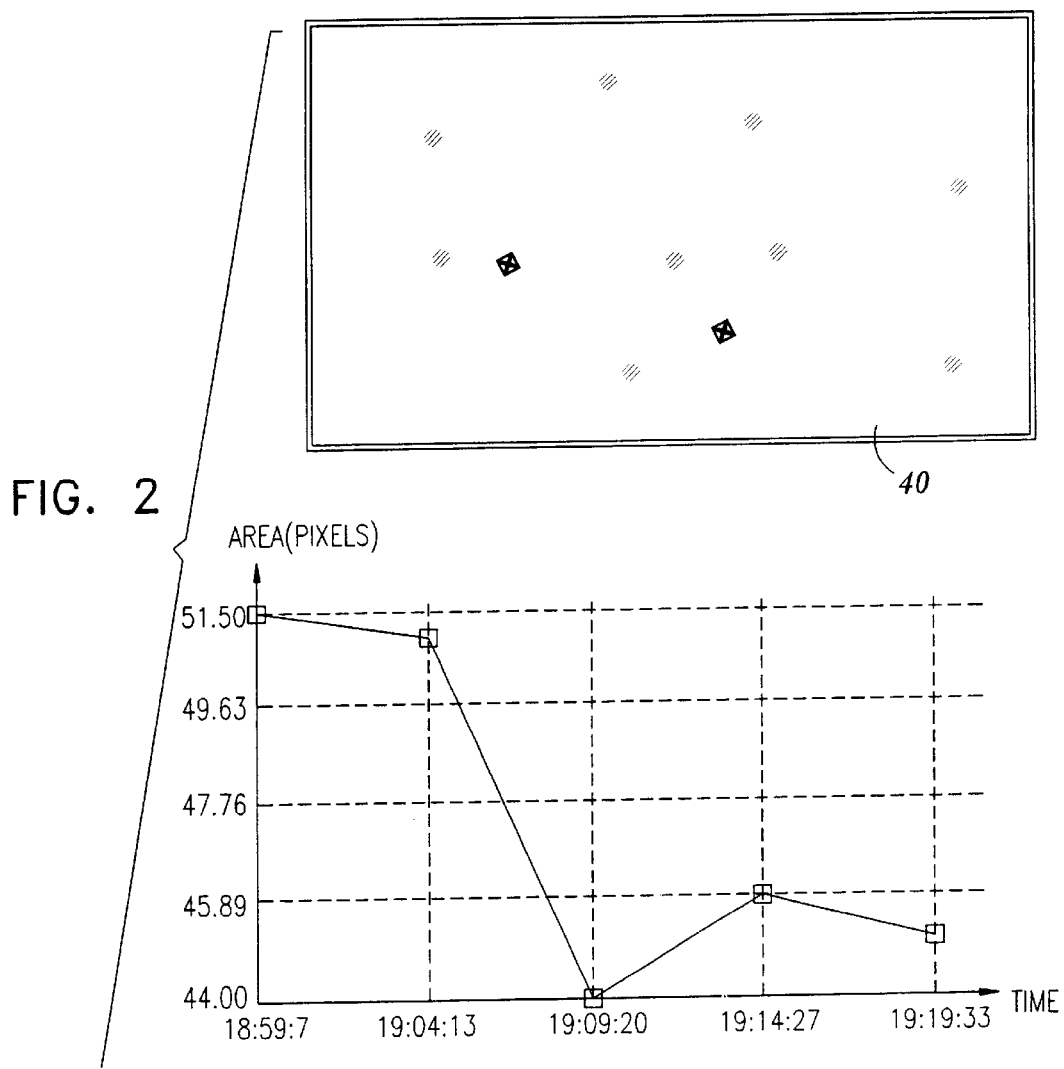
FIG. 2 is an illustration of a typical image analysis report provided by the system and method of FIG. 1.

Reference is now made to FIG. 2 which is an illustration of a typical image analysis report provided by the system and method of FIGS. 1 and 3. The report of FIG. 2 preferably includes an image 40 showing calcium oxalate crystals as viewed by the video camera 20 (FIG. 1) together with tabular information 42 relating to the area, brightness, perimeter, compactness, number of holes and roughness of the crystals at various times. Also preferably included in the report of FIG. 2 are graphs which indicate the time variation of various ones of the above parameters. The foregoing information may then be used to arrive at an indication of the propensity of a subject to formation of urinary stones. Preferably, the software of the present invention may itself provide an indication of the effectiveness of inhibition of crystallization of calcium oxalate salts in the examined urine, as shown at reference numeral 44.

Figure 4:
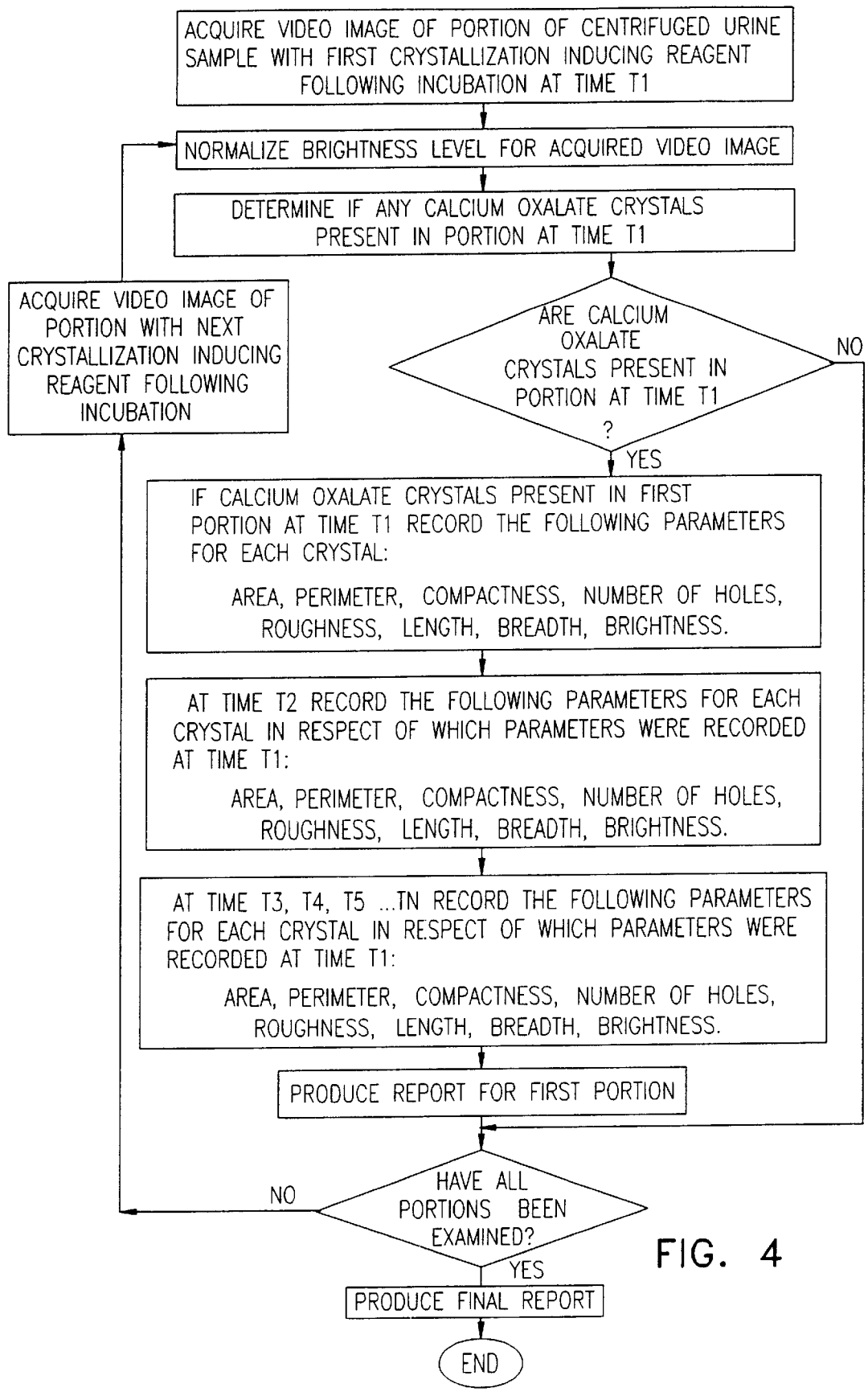
FIGS. 4, 5 and 6 are each simplified flowcharts illustrating constituents of the functional features of the flowchart of FIG. 3.

Reference is now made to FIG. 4, which is a generalized flowchart illustrating the image analysis carried out by the present invention. As seen in FIG. 4, a video image is acquired of a first portion of a centrifuged urine sample containing a first crystallization inducing reagent following incubation at time T1. Preferably, the first crystallization inducing reagent is the lowest concentration reagent.

The brightness level of the acquired video image is normalized and a determination is made as to whether any calcium oxalate crystals are present in the first portion at time T1.

If no calcium oxalate crystals are present in the first portion at time T1, the above procedure is carried out for each of the subsequent portions, containing reagents at increasing concentrations, until a portion containing such crystals is encountered. If no portion containing calcium oxalate crystals is encountered, a report is prepared indicating effectiveness of inhibition of crystallization of calcium oxalate salts in the examined urine.

If however, calcium oxalate crystals are found in a portion at time T1, the following parameters are recorded for each crystal:

AREA
PERIMETER
COMPACTNESS
NUMBER OF HOLES
ROUGHNESS
LENGTH
BREADTH
BRIGHTNESS

Thereafter, at time T2, typically 5 minutes following time T1, the above parameters are again recorded for each crystal which was present and inspected at time T1.

This procedure is repeated at times T3, T4 . . . TN, where N preferably is equal to 7, each time preferably being separated from the preceding time by approximately 5 minutes.

A report, preferably containing the content appearing in FIG. 2, is prepared for the portion in which calcium oxalate crystals are encountered.

Figure 5:
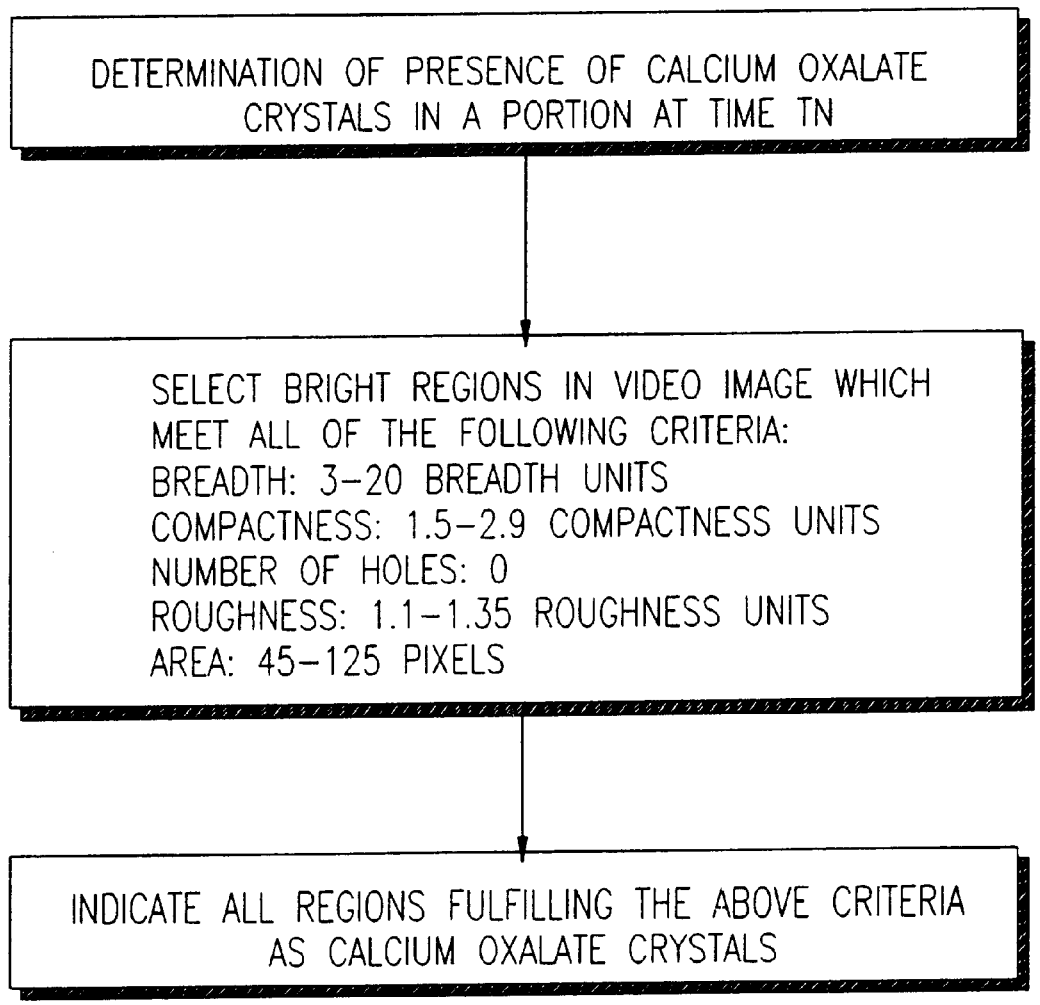

Reference is now made to FIG. 5, which illustrates the methodology of determination of the presence of calcium oxalate crystals in a portion, in the technique of FIG. 4.

As seen in FIG. 5, there is provided selection of bright regions in the video image which meet all of the following criteria:

BREADTH: 3–20 BREADTH UNITS
COMPACTNESS: 1.5–2.9 COMPACTNESS UNITS
NUMBER OF HOLES: 0
ROUGHNESS: 1.1–1.35 ROUGHNESS UNITS
AREA: 45–125 PIXELS

All bright regions fulfilling the above criteria are identified as calcium oxalate crystals.

Figure 6:
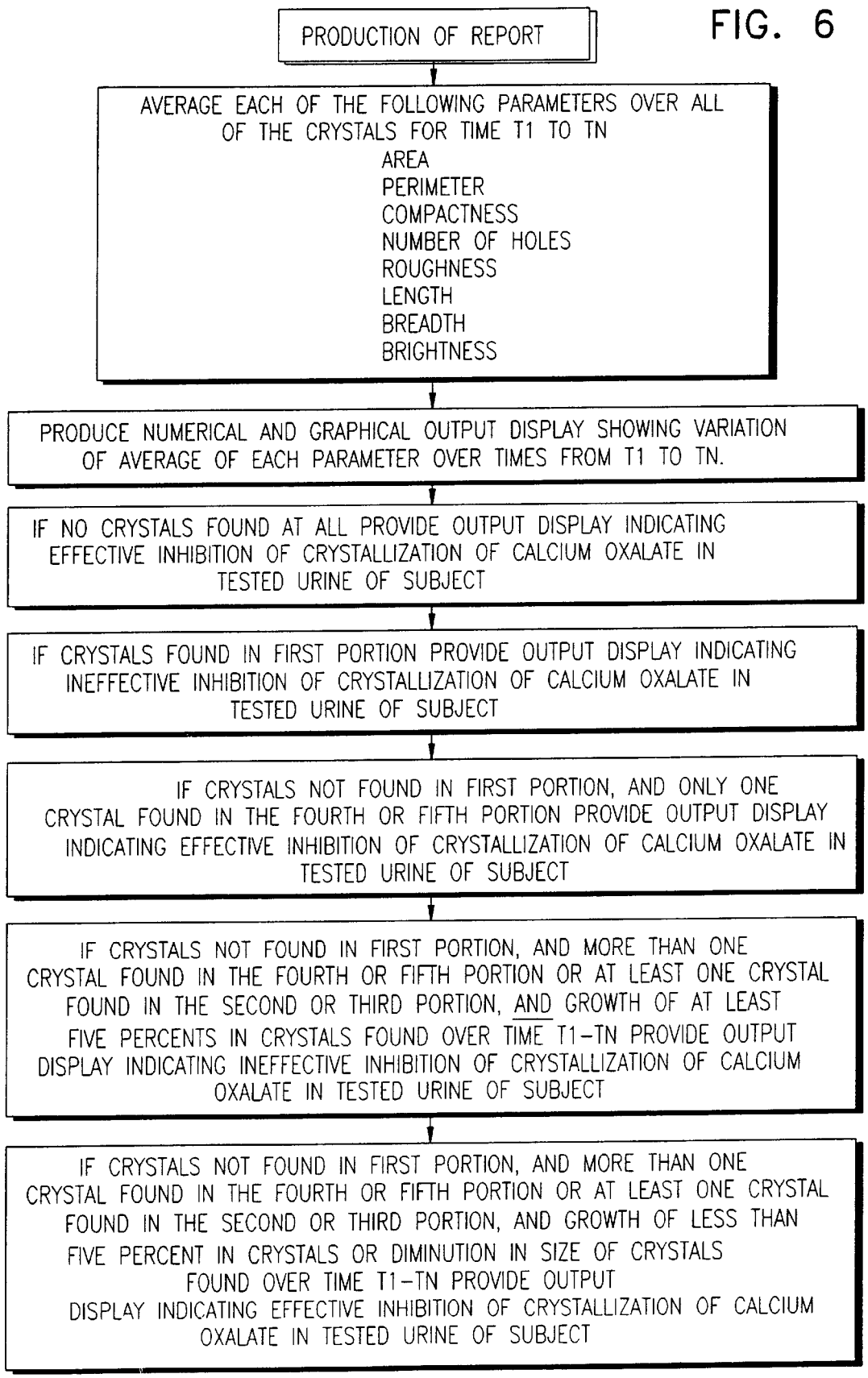

Reference is now made to FIG. 6, which illustrates the methodology of preparing a report such as the report illustrated in FIG. 2.

As indicated in FIG. 6, each of the following parameters is averaged over all of the crystals in the video image of a portion at time TN:

AREA
PERIMETER
COMPACTNESS
NUMBER OF HOLES
ROUGHNESS
LENGTH
BREADTH
BRIGHTNESS

A numerical and graphical output display showing the variation of the average of each parameter over times from T1 to TN is prepared.

As indicated above, if no portion containing calcium oxalate crystals is encountered, a report is prepared indicating effectiveness of inhibition of crystallization of calcium oxalate salts in the examined urine.

If calcium oxalate crystals are found in the first portion, a report is prepared indicating ineffective inhibition of crystallization of calcium oxalate salts in the examined urine.

If, however, crystals are not found in the first portion and only one crystal is found in fourth or fifth portion, a report is prepared indicating effective inhibition of crystallization of calcium oxalate salts in the examined urine.

Should crystals not be found in the first portion and more than one crystal be found in the fourth or fifth portion or at least one crystal be found in the second or third portion, and growth of at least five percent be found in the crystals over time T1–TN, a report is prepared indicating ineffective inhibition of crystallization of calcium oxalate salts in the examined urine.

A preferred method for constructing a system for indicating the propensity of a subject to formation of urinary stones operative in accordance with a preferred embodiment of the present invention is now described with reference to Appendix A:

a) Provide a computer terminal configured with the Microsoft Windows 95 operating system;

b) Install the Matrox Inspector 2.1 software described hereinabove on the computer terminal provided in step a) in a directory named \Insptr;

c) Generate the binary file TmpD11.dll from the portion of the hexadecimal software listing of Appendix A labeled "hex_code.txt", and the binary file Project-New.scr and from the portion labeled "Project-New.scr";

d) Load the files generated in step c) into a subdirectory of \Insptr named \Project;

e) Execute the program Insptr32.exe in the \Insptr directory and double-click on the last available project icon.

It is appreciated that any of the software components of the present invention may, if desired, be implemented in ROM (read-only memory) form. The software components may, generally, be implemented in hardware, if desired, using conventional techniques.

It is appreciated that the particular embodiment described in Appendix A is intended only to provide an extremely detailed disclosure of the present invention and is not intended to be limiting.

It will be appreciated by persons skilled in the art that the present invention is not limited to what has been specifically shown and described hereinabove. Rather the scope of the present invention includes both combinations and subcombinations of the various features described hereinabove as well as modifications thereof which would occur to persons skilled in the art upon reading the foregoing description and which are not in the prior art.

What is claimed is:

1. Apparatus for indicating the propensity of a subject to formation of urinary stones comprising:

apparatus for optically observing a urine sample from a subject under magnification; and an image analyzer operative to determine the existence of crystalline bodies in said urine sample and to provide an output indication thereof and wherein said image analyzer includes software which measures the mass of said crystalline bodies.

2. Apparatus for indicating the propensity of a subject to formation of urinary stones comprising:

apparatus for optically observing a urine sample from a subject under magnification; and an image analyzer operative to determine the existence of crystalline bodies in said urine sample and to provide an output indication thereof and wherein said image analyzer includes software which indicates changes in said crystalline bodies over time.

3. Apparatus for analyzing the urine of a subject comprising: apparatus for optically observing a urine sample from a subject under magnification; and an image analyzer operative to determine the existence of bodies in said urine sample and to provide an output indication thereof, wherein said image analyzer includes software which measures the mass of said bodies.

4. Apparatus for analyzing the urine of a subject comprising: apparatus for optically observing a urine sample from a subject under magnification; and an image analyzer operative to determine the existence of bodies in said urine sample and to provide an output indication thereof, wherein said image analyzer includes software which indicates changes in said bodies over time.

5. A method for indicating the propensity of a subject to formation of urinary stones comprising:

optically observing a urine sample from a subject under magnification;

performing computerized image analysis to determine the existence of crystalline bodies in said urine sample and to provide an output indication thereof, and wherein said step of optically observing a urine sample is operative to observe at least one urine sample in the presence of at least one reagent, and wherein said at least-one reagent comprises a crystallization inducer and correlating a concentration of said crystallization inducer to said subject's propensity to form urinary stones.

6. A method for analyzing the urine of a subject comprising: optically observing a urine sample from a subject under magnification, wherein said step of optically observing a urine sample is operative to observe at least one urine sample in the presence of at least one reagent, and wherein said optically observing a urine sample is operative to observe a plurality of urine samples from a subject in the presence of a plurality of different reagents; and performing image analysis to determine the existence of bodies in said urine sample and to provide an output indication thereof and wherein said bodies include at least one of cells, crystalline bodies, microorganisms and casts, and wherein said image analysis measures the mass of said bodies.

7. A method for analyzing the urine of a subject comprising: optically observing a urine sample from a subject under magnification, wherein said step of optically observing a urine sample is operative to observe at least one urine sample in the presence of at least one reagent, and wherein said optically observing a urine sample is operative to observe a plurality of urine samples from a subject in the presence of a plurality of different reagents; and performing image analysis to determine the existence of bodies in said urine sample and to provide an output indication thereof and wherein said bodies include at least one of cells, crystalline bodies, microorganisms and casts, and wherein said image analysis indicates changes in said bodies over time.

* * * * *